US012708276B2

(12) United States Patent
Tokko

(10) Patent No.: US 12,708,276 B2
(45) Date of Patent: Aug. 18, 2026

(54) BLOOD PRESSURE MEASUREMENT DEVICE

(71) Applicant: OMRON HEALTHCARE Co., Ltd., Kyoto (JP)

(72) Inventor: Yoshihide Tokko, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 288 days.

(21) Appl. No.: 18/487,705

(22) Filed: Oct. 16, 2023

(65) Prior Publication Data

US 2024/0041337 A1 Feb. 8, 2024

Related U.S. Application Data

(63) Continuation of application No. PCT/JP2022/020345, filed on May 16, 2022.

(30) Foreign Application Priority Data

May 19, 2021 (JP) ................................ 2021-084581

(51) Int. Cl.
*A61B 5/022* (2006.01)
*A61B 5/00* (2006.01)

(52) U.S. Cl.
CPC .......... *A61B 5/02233* (2013.01); *A61B 5/681* (2013.01); *A61B 5/742* (2013.01); *A61B 2560/0443* (2013.01)

(58) Field of Classification Search
CPC ............................ A61B 5/02233; A61B 5/681
See application file for complete search history.

(56) References Cited

U.S. PATENT DOCUMENTS 4,896,676 A * 1/1990 Sasaki ................ A61B 5/02241 600/494
2016/0034696 A1* 2/2016 Jooste ..................... G06F 1/163 726/1

(Continued)

FOREIGN PATENT DOCUMENTS

CN 110267588 A1 9/2019
CN 211934039 U 11/2020

(Continued)

OTHER PUBLICATIONS

International Preliminary Report on Patentability for International Application No. PCT/JP2022/020345, Dated Dec. 28, 2022.

(Continued)

*Primary Examiner* — Daniel L Cerioni
(74) *Attorney, Agent, or Firm* — Colson Law Group, PLLC

(57) ABSTRACT

A blood pressure measurement device includes: a watch body including a first display unit configured to display information including a time and a blood pressure value and disposed on a back side of a wrist; a band including a pressure measurement unit including a pump and a pressure sensor configured to detect a pressure, and band portions provided at symmetrical positions in a circumferential direction of an outer circumferential surface of the pressure measurement unit, connected to the watch body, and extending from the pressure measurement unit, the band configured to fix the watch body to the wrist; a cuff structure fluidly connected to the pump and in which pressure is detected by the pressure sensor; and a first control unit provided in the watch body or the pressure measurement unit and configured to calculate a blood pressure value based on a detection result of the pressure sensor.

7 Claims, 16 Drawing Sheets

(56) References Cited

U.S. PATENT DOCUMENTS

2019/0290140 A1* 9/2019 Higashimura ..... A61B 5/02141
2019/0290143 A1* 9/2019 Iwata ................. A61B 5/02233
2019/0365259 A1* 12/2019 Nishikawa ......... A61B 5/02233
2019/0387977 A1* 12/2019 Shimizu ................... A61B 5/25
2022/0233085 A1* 7/2022 Lee .................... A61B 5/02233

FOREIGN PATENT DOCUMENTS

JP 11-342118 A 12/1999
JP 2017-529883 A 10/2017
JP 2018-121829 A 8/2018
JP 2019-118418 A 7/2019
JP 2020-62088 A 4/2020
JP 2020-103639 A 7/2020
KR 10-2020-0141244 A 12/2020

OTHER PUBLICATIONS

International Search Report (ISR) for International Application No. PCT/JP2022/020345, Dated Jul. 12, 2022.
International Preliminary Report (IPRP) for International Application No. PCT/JP2022/020345, Dated Dec. 28, 2022.
Chinese Office Action for application No. 202280028344.6 dated Mar. 7, 2026.

* cited by examiner

[FIG. 1]
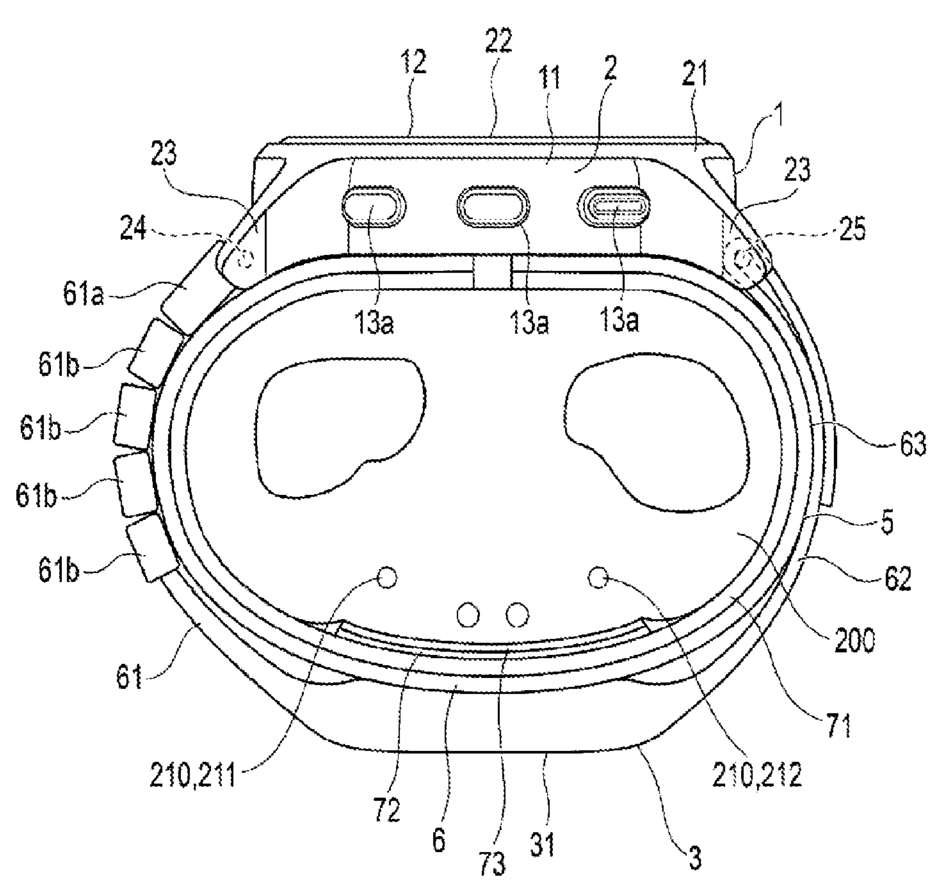

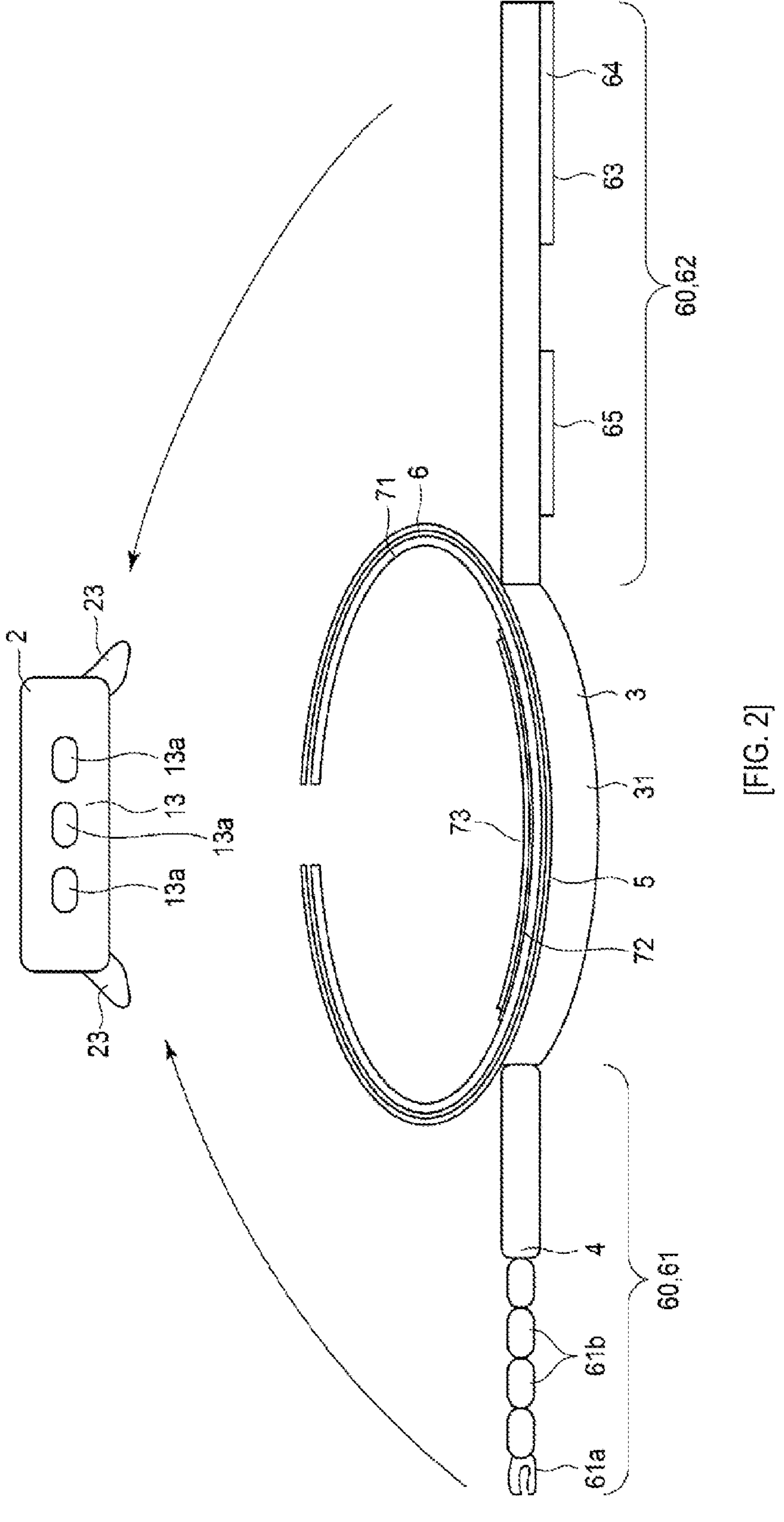
[FIG. 2]

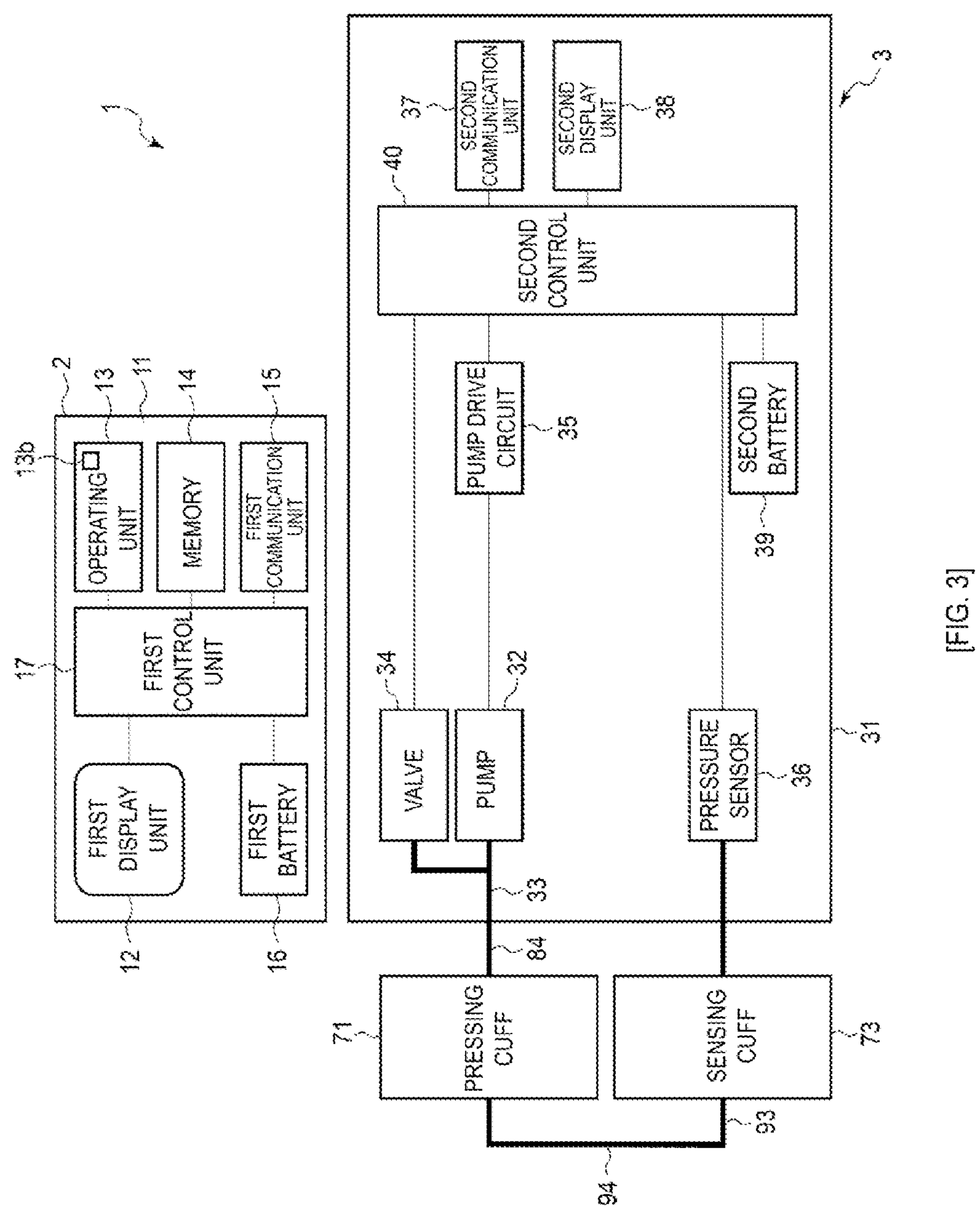
[FIG. 3]

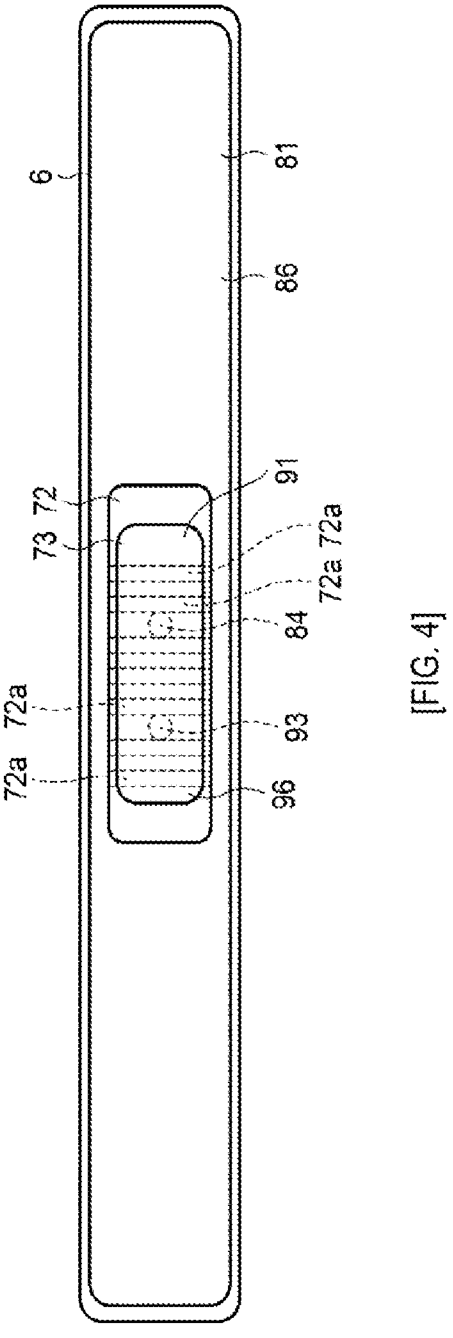
[FIG. 4]

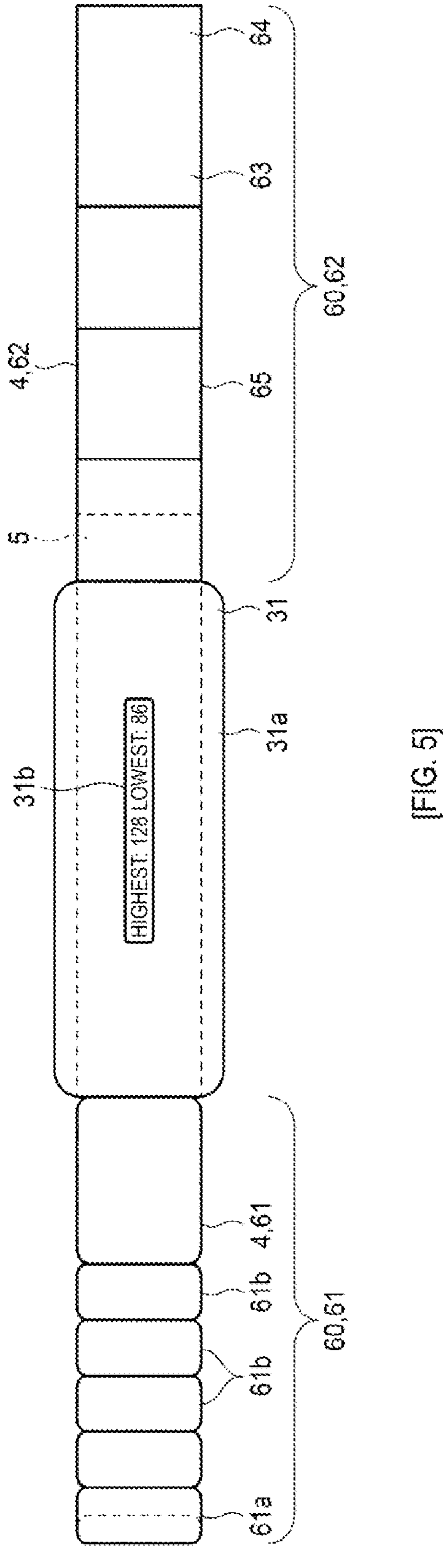
[FIG. 5]

[FIG. 7]
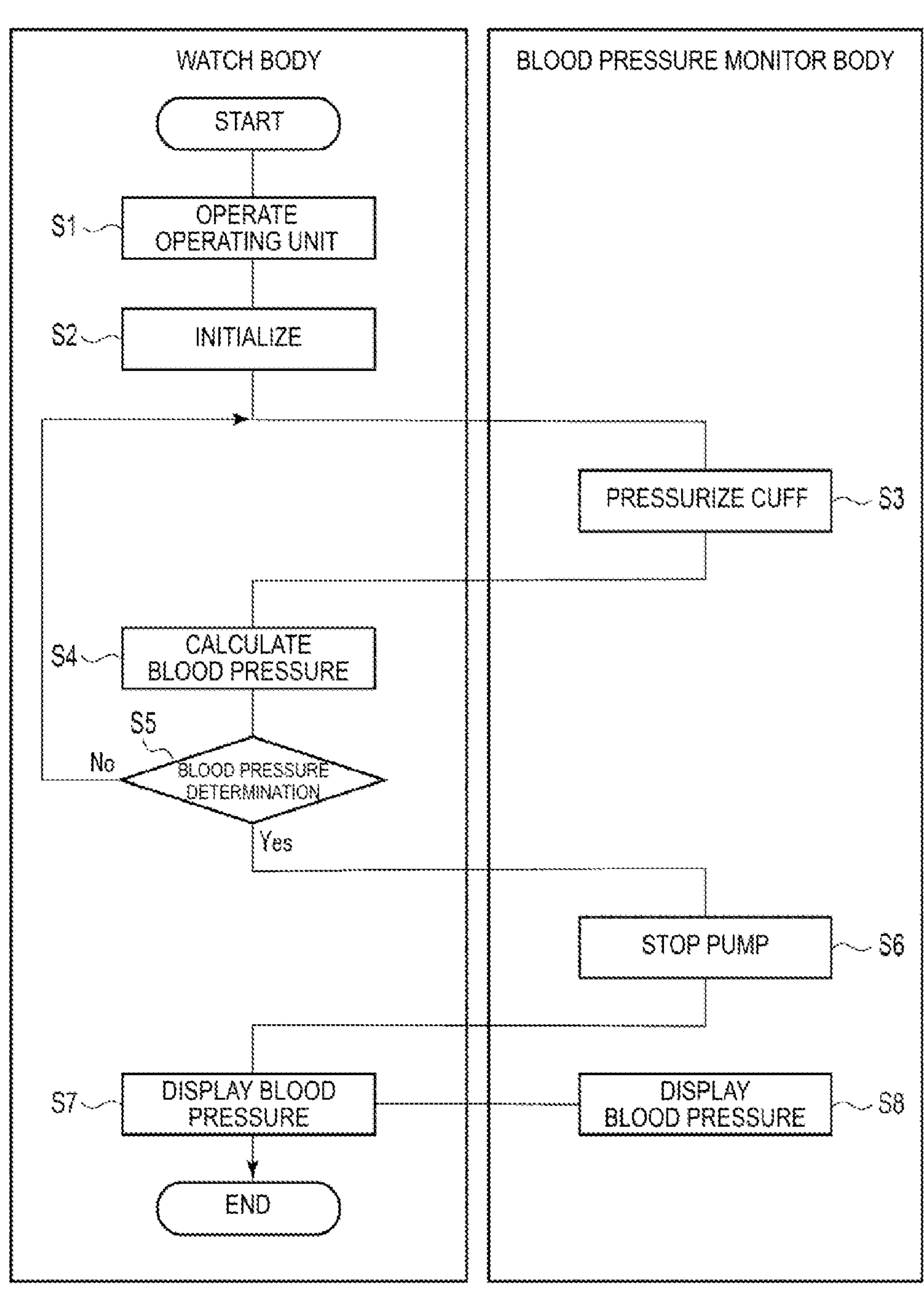

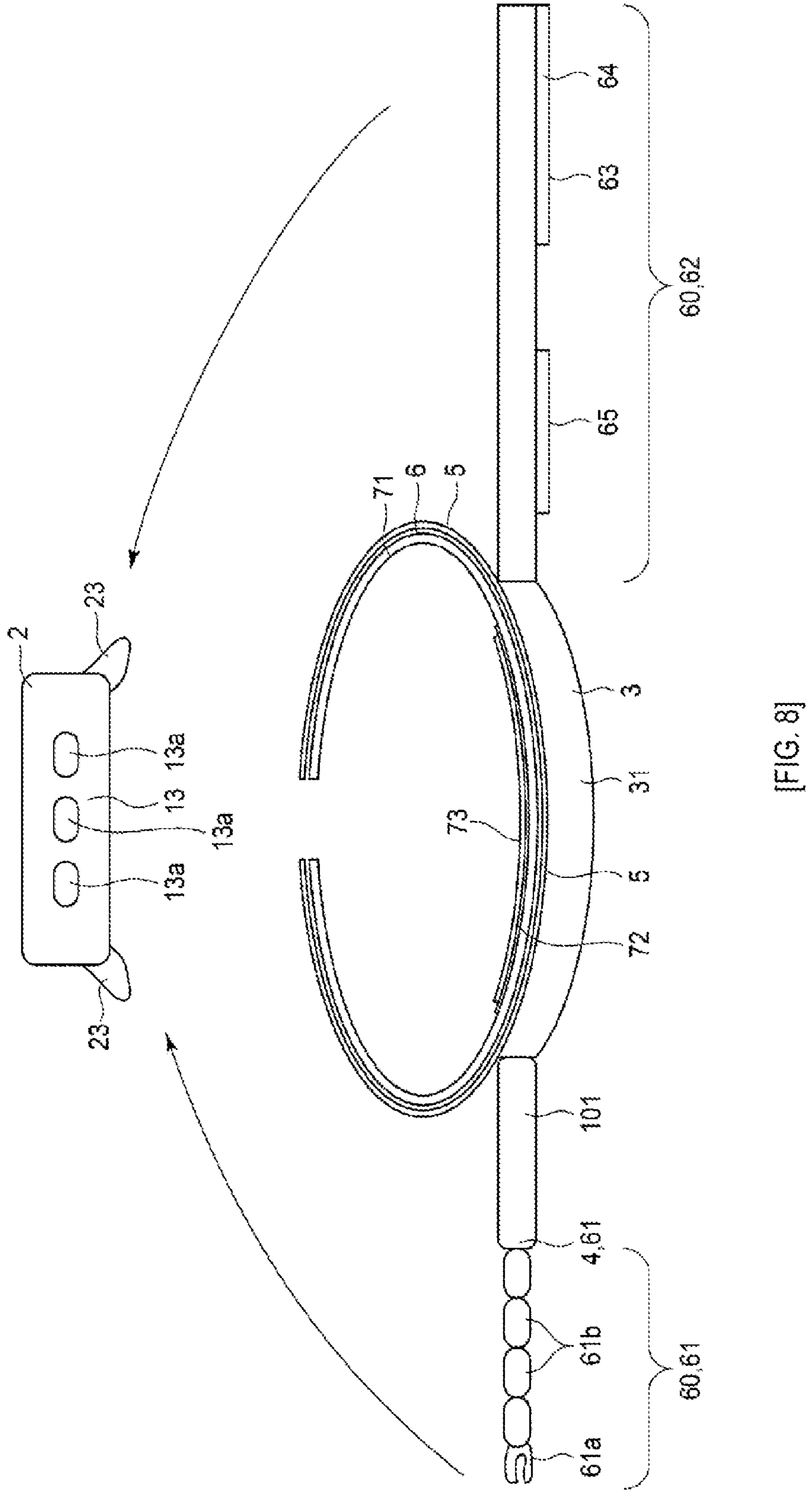
[FIG, 8]

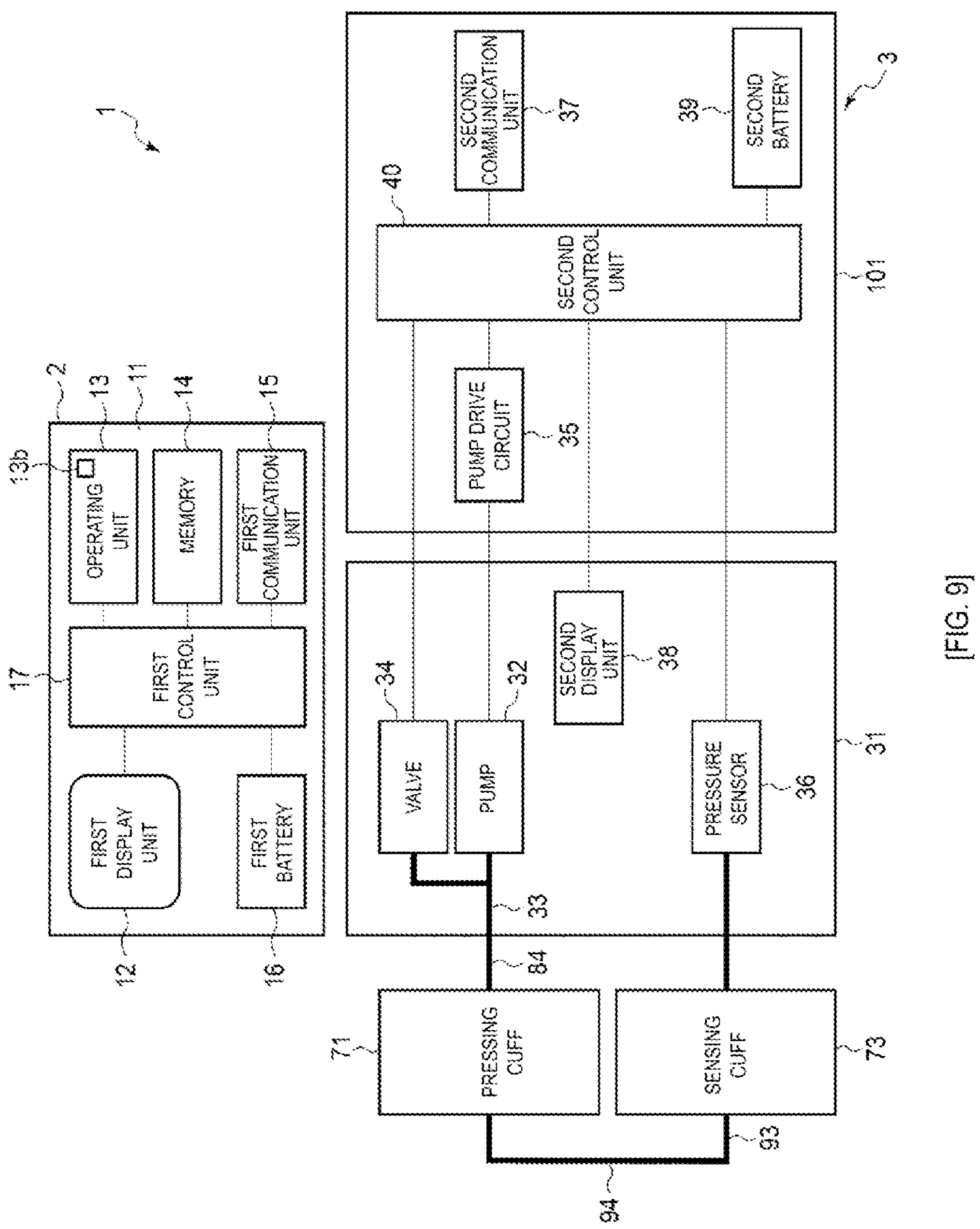
[FIG. 9]

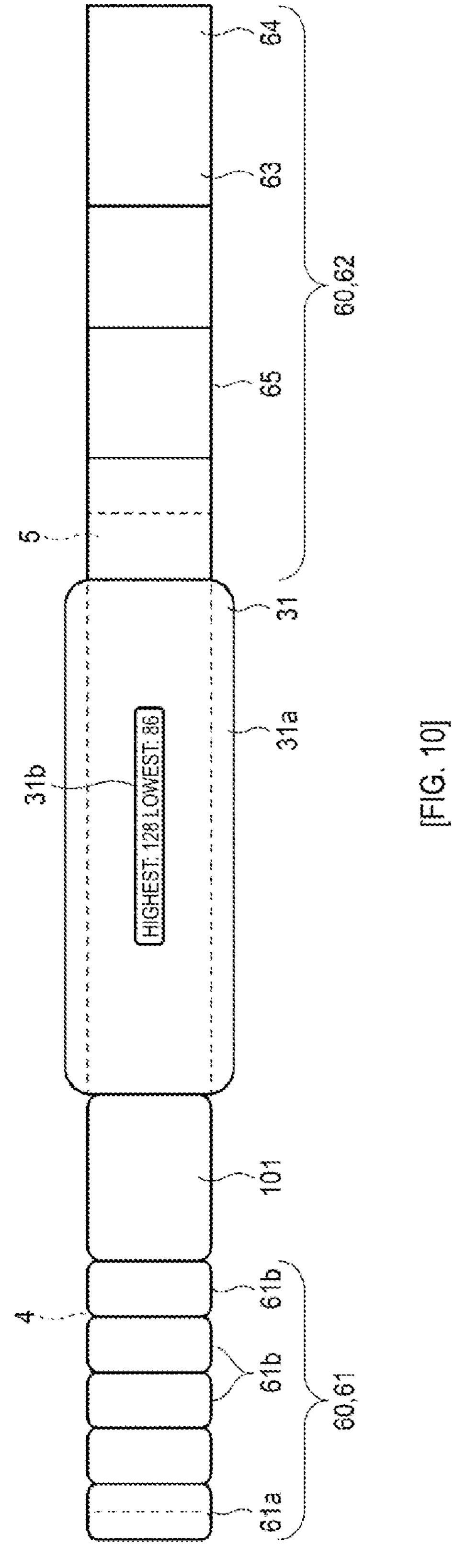
[FIG. 10]

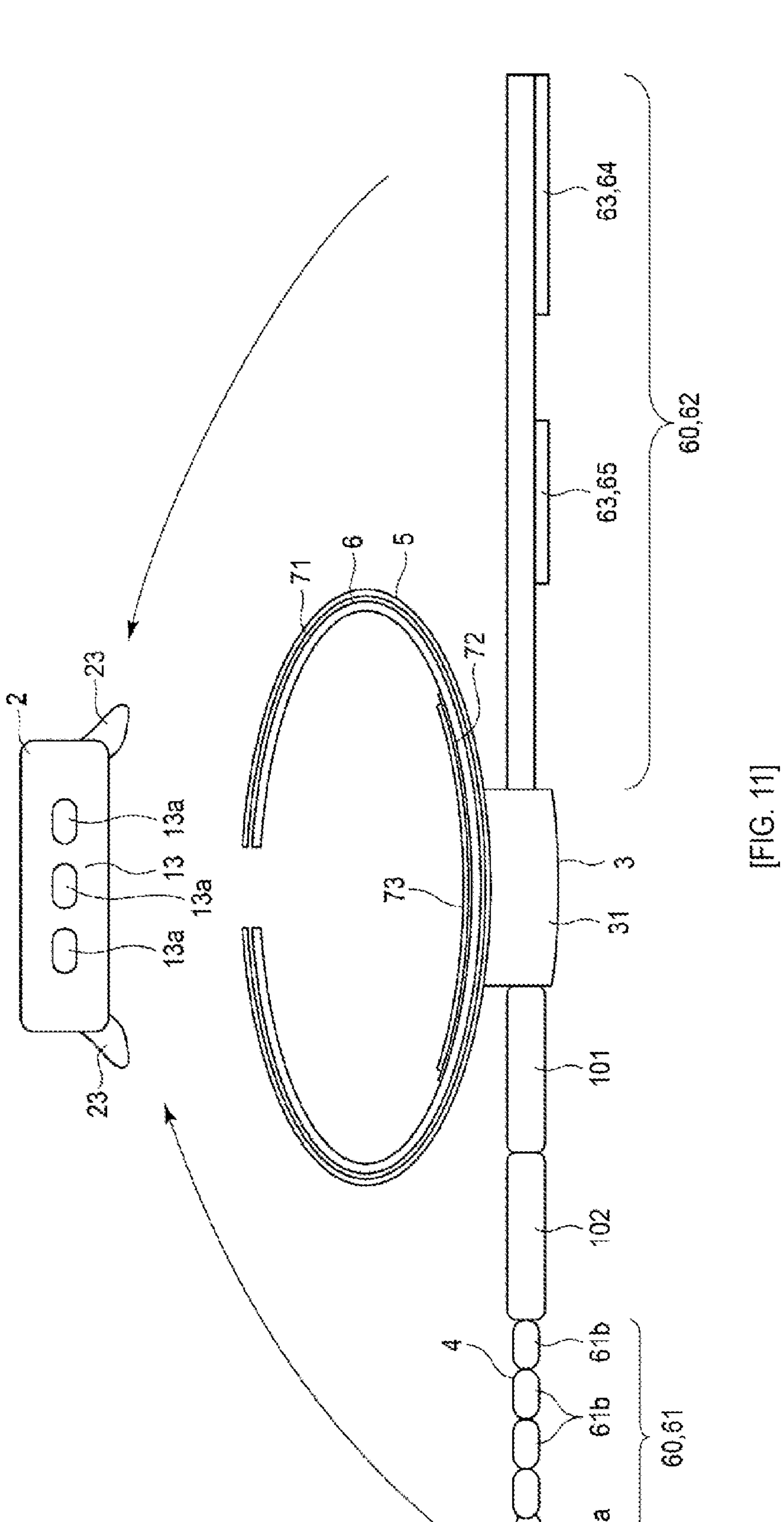
[FIG. 11]

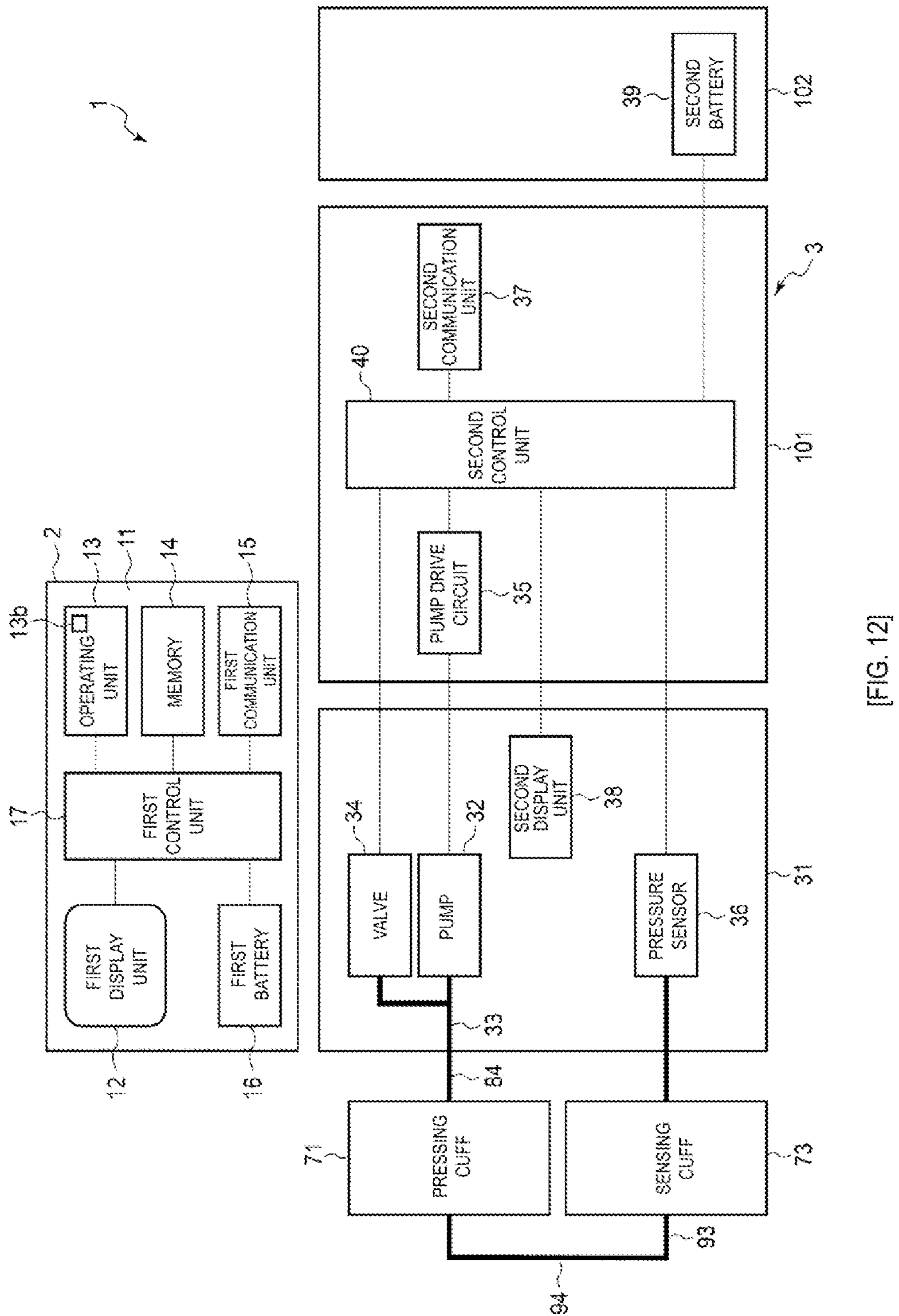
[FIG. 12]

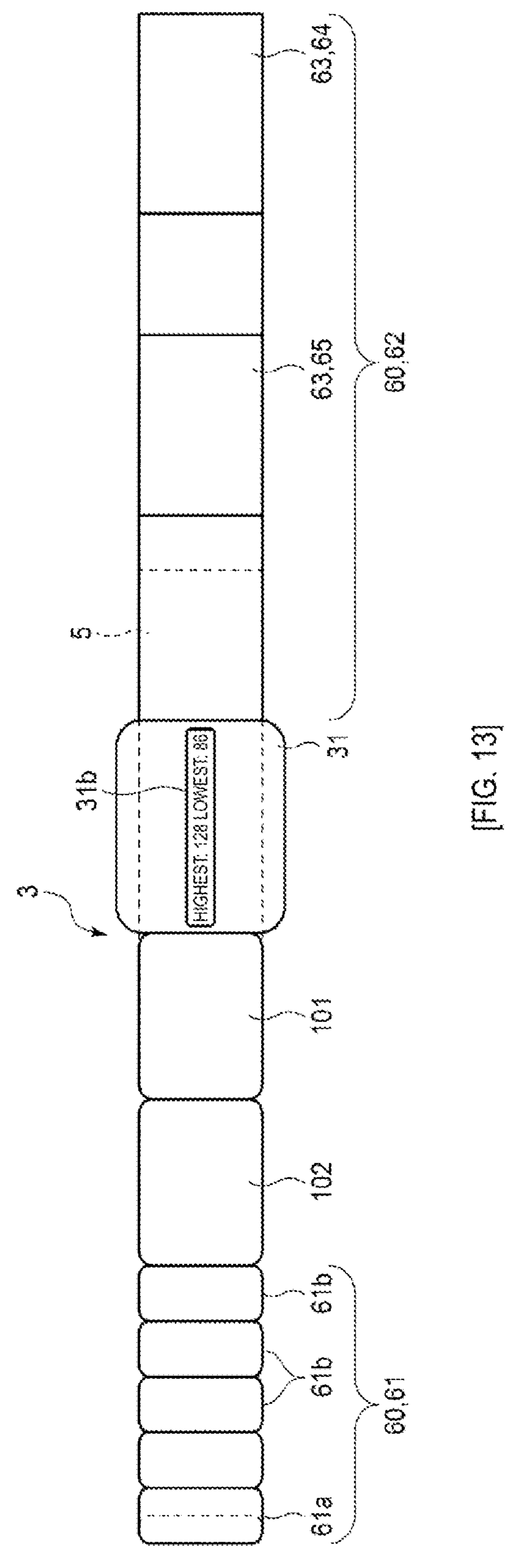
[FIG. 13]

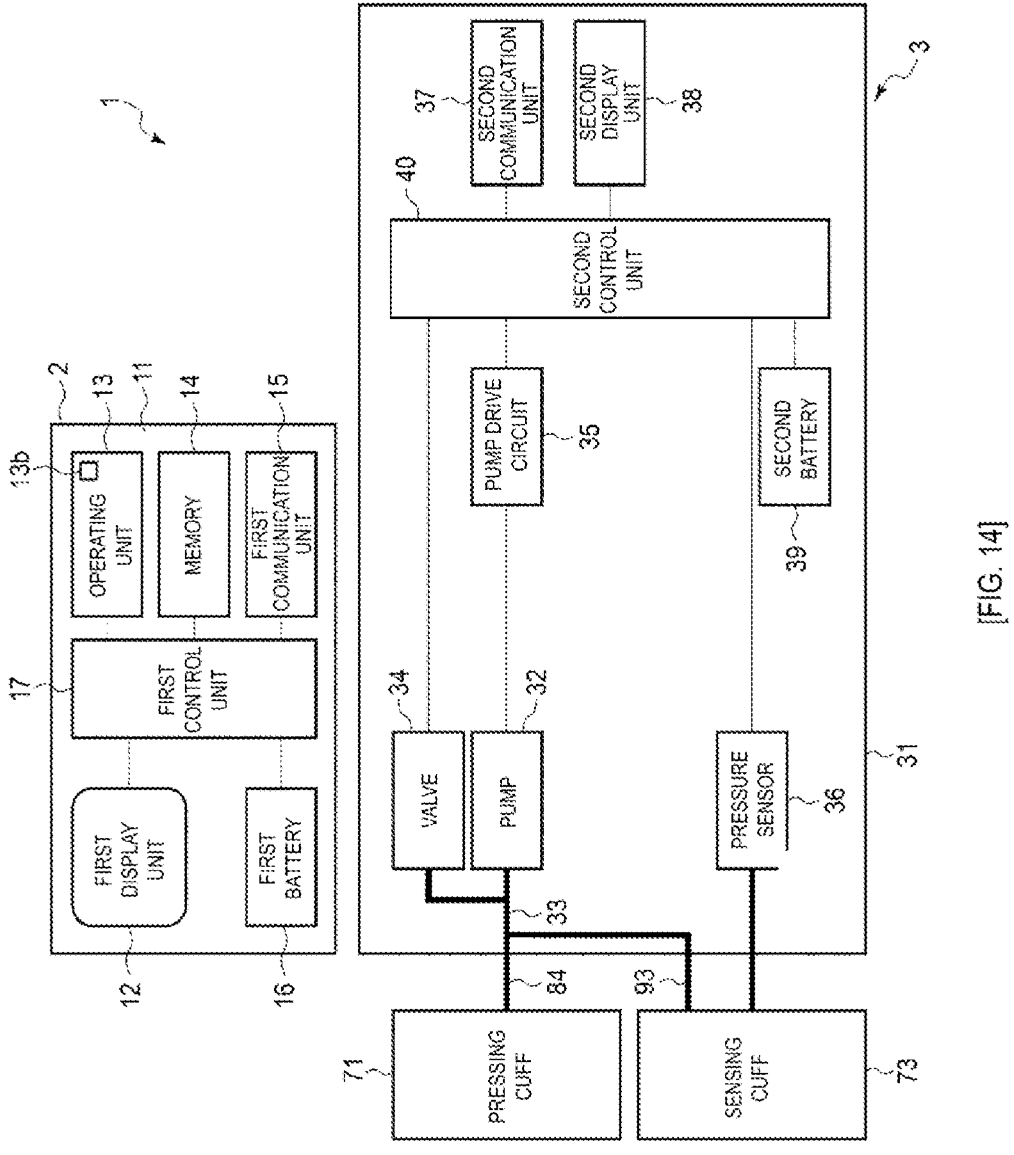
[FIG. 14]

[FIG. 15]
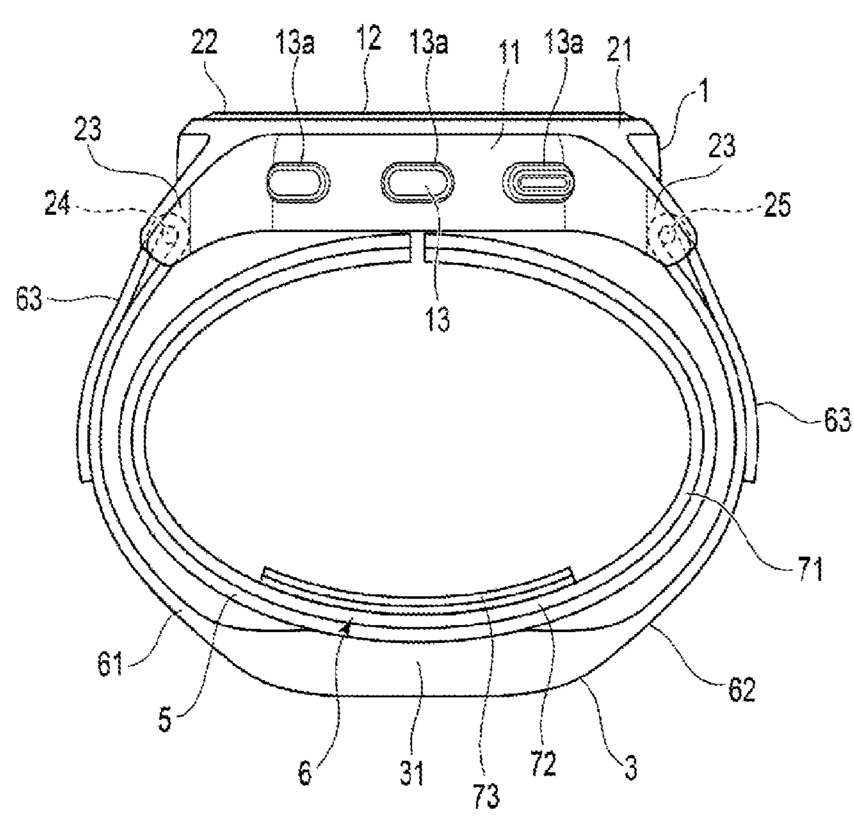

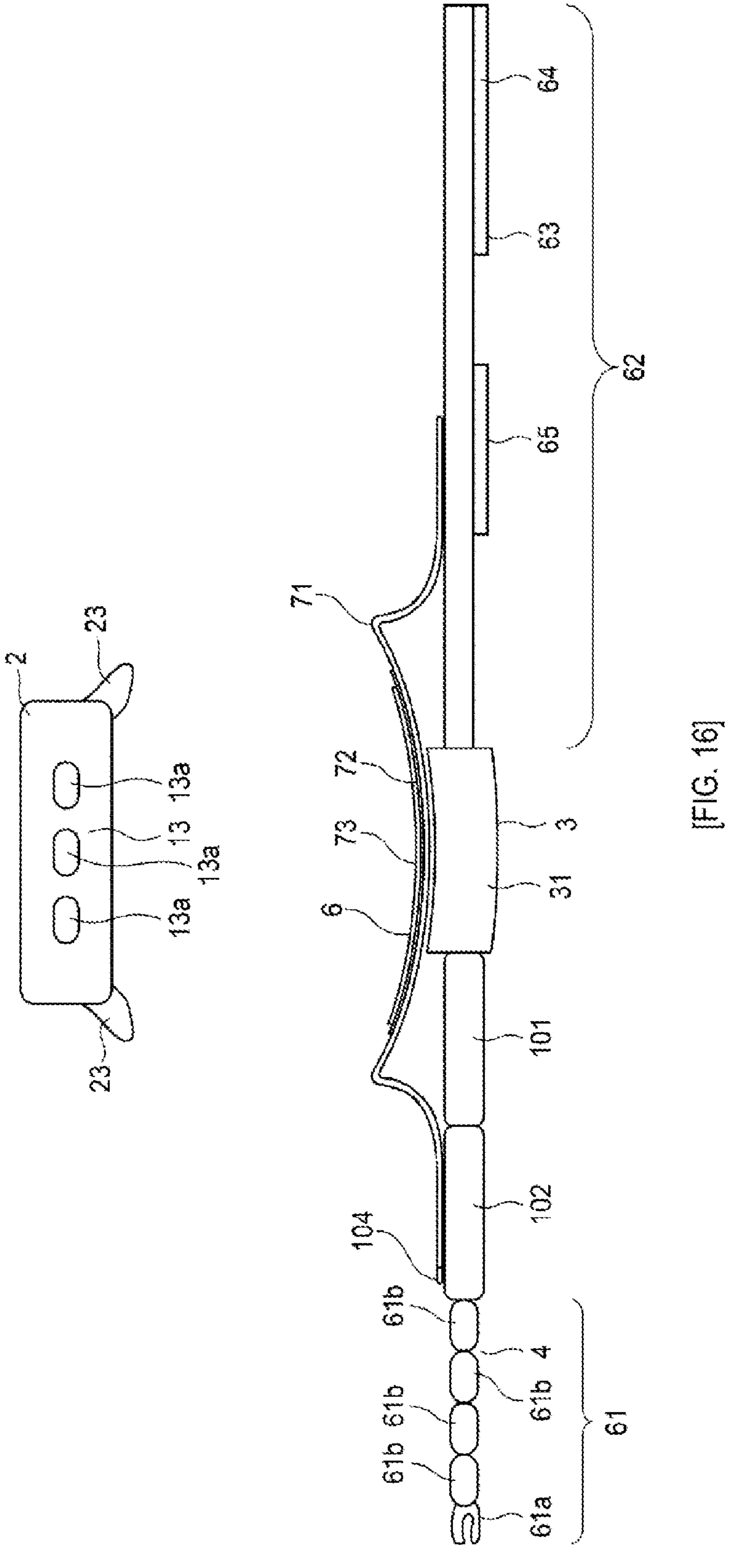
[FIG. 16]

BLOOD PRESSURE MEASUREMENT DEVICE

CROSS-REFERENCE TO RELATED APPLICATIONS

This application is the U.S. national stage application filed pursuant to 35 U.S.C. 365(c) and 120 as a continuation of International Patent Application No. PCT/PCT/JP2022/020345, filed May 16, 2022, which application claims priority to Japanese Patent Application No. 2021-084581, filed May 19, 2021, which applications are incorporated herein by reference in their entireties.

TECHNICAL FIELD

The present invention relates to a blood pressure measurement device.

BACKGROUND ART

In recent years, blood pressure measurement devices used for measuring a blood pressure are being used as means to check health status at home, as well as in medical facilities. A blood pressure measurement device detects vibration of the artery wall to measure blood pressure by, for example, inflating and contracting a cuff wound around the upper arm, the wrist, or the like of a living body and detecting the pressure in the cuff by using a pressure sensor.

As such a blood pressure measurement device, a so-called integral type is known in which a cuff is integrated with a device body feeding a fluid to the cuff. This type of the blood pressure measurement device is known to include a device body that incorporates a blood pressure measurement pump and a pressure sensor and is disposed on a back side of a hand when worn on a wrist, a band that fixes the blood pressure measurement device to the wrist, a pressing cuff that is disposed on an inner peripheral side of the band and extends along a circumferential direction of the wrist, and a sensing cuff that is disposed on the inner peripheral side of the pressing cuff and in a region where a wrist artery exists. For example, in the blood pressure measurement device described in JP 2019-118418 A, the wrist is compressed by the pressing cuff and the sensing cuff, and the blood pressure is measured based on a pressure of a pressure-transmitting fluid contained in the sensing cuff.

CITATION LIST

Patent Literature

Patent Document 1: JP 2019-118418 A

SUMMARY OF INVENTION

Technical Problem

In the blood pressure measurement device described in Patent Document 1, since the device body is disposed on the back side of the hand, by mounting a function of displaying the time on the device body, the device is suitable for an application in which the device is always worn as a wristwatch. However, since it is necessary to fluidly connect the cuff to the device body disposed on the back side of the hand, there is a problem in that the structure becomes complicated and the manufacturing load increases.

Therefore, an object of the present invention is to provide a blood pressure measurement device in which a configuration for exerting a function of displaying information and a configuration for exerting a function of measuring a blood pressure value are separated.

Solution to Problem

According to an aspect of the invention, there is provided a blood pressure measurement device to be worn on a wrist of a user, the blood pressure measurement device including: a watch body including a display unit and a first communication unit, the display unit being configured to display information including time and a blood pressure value, the watch body being disposed on a back side of the wrist; a band including a pressure measurement unit and a band portion, the pressure measurement unit including a second communication unit configured to communicate with the first communication unit, a pump, and a sensor configured to detect a pressure, the band portion being provided in the pressure measurement unit and connected to the watch body; a cuff provided on the band and fluidly connected to the pump and the sensor; and a control unit provided in the watch body or the pressure measurement unit and configured to calculate a blood pressure value based on a detection result of the sensor.

Here, the cuff is inflated by being supplied with a fluid, and includes a bag-like structure such as an air bag.

According to this aspect, since the blood pressure measurement device is configured to include the watch body and the band which includes the pressure measurement unit and is connected to the watch body, a configuration for exerting a function of displaying information and a configuration for exerting a function of measuring a blood pressure value can be separated.

In the blood pressure measurement device according to the aspect, there is provided the blood pressure measurement device wherein the cuff includes a sensing cuff disposed in a region where an artery of the wrist exists, and the sensing cuff is disposed on a side of the wrist of the pressure measurement unit.

According to this aspect, by using the pressure measurement unit as a mark, the sensing cuff can be easily disposed in the region of the wrist where the artery exists.

In the blood pressure measurement device according to the aspect, there is provided the blood pressure measurement device wherein the band is detachably attached to the watch body.

According to this aspect, the pressure measurement unit can be attached to a different watch body.

In the blood pressure measurement device according to the aspect, there is provided the blood pressure measurement device wherein the band portion is configured such that a length between the pressure measurement unit and the watch body can be adjusted.

According to this aspect, by adjusting the length of the band portion, it is possible to dispose the watch body on the back side of the wrist and dispose the pressure measurement unit on a palm side of the wrist according to the circumferential length of the wrist of the user. Since the band can be suitably tightened in accordance with the circumferential length of the wrist, the accuracy of blood pressure measurement can be improved.

In the blood pressure measurement device according to the aspect, there is provided the blood pressure measurement device wherein the control unit is provided in the watch body.

According to this aspect, since the pressure measurement unit does not need to have a function of calculating the blood pressure value, the pressure measurement unit can be miniaturized.

In the blood pressure measurement device according to the aspect, there is provided the blood pressure measurement device wherein the pressure measurement unit includes a pressure measurement unit display unit configured to display a blood pressure value.

According to this aspect, the blood pressure value can be visually recognized by the pressure measurement unit.

In the blood pressure measurement device according to the aspect, there is provided the blood pressure measurement device wherein the watch body or the pressure measurement unit includes an operating unit to which operation of starting blood pressure measurement is input.

According to this aspect, the operability of the operating unit can be improved.

Advantageous Effects of Invention

The present invention can provide a blood pressure measurement device in which a watch body for displaying information including time and a blood pressure value and a blood pressure measurement unit for measuring a pressure for blood pressure measurement are separated.

BRIEF DESCRIPTION OF DRAWINGS

Various embodiments are disclosed, by way of example only, with reference to the accompanying schematic drawings in which corresponding reference symbols indicate corresponding parts, in which:

FIG. 1 is an explanatory view illustrating a configuration of a blood pressure measurement device according to an embodiment of the present invention in a state of being worn on a wrist.

FIG. 2 is a side view illustrating a state in which a band and a pressure measurement unit used in the blood pressure measurement device are separated from a watch body used in the blood pressure measurement device.

FIG. 3 is a block diagram illustrating the configuration of the blood pressure measurement device.

FIG. 4 is a plan view illustrating a configuration of a cuff structure used in the blood pressure measurement device.

FIG. 5 is a plan view illustrating the configuration of the pressure measurement unit and the band as viewed from a side opposite to the wrist side.

FIG. 6 is an explanatory view illustrating a state in which the blood pressure measurement device is worn on a wrist.

FIG. 7 is a flowchart illustrating an example of operation of the blood pressure measurement device.

FIG. 8 is a side view illustrating a configuration of a modification of the blood pressure measurement device.

FIG. 9 is a block diagram illustrating a configuration of the blood pressure measurement device.

FIG. 10 is a plan view illustrating the pressure measurement unit and the band used in the blood pressure measurement device as viewed from the side opposite to the wrist side.

FIG. 11 is a side view illustrating the configuration of the blood pressure measurement device according to the modification of the present invention.

FIG. 12 is a block diagram illustrating the configuration of the blood pressure measurement device.

FIG. 13 is a plan view illustrating the pressure measurement unit and the band used in the blood pressure measurement device as viewed from the side opposite to the wrist side.

FIG. 14 is a block diagram illustrating the configuration of the blood pressure measurement device according to the modification of the present invention.

FIG. 15 is a side view illustrating the arrangement of the blood pressure measurement device according to the modification of the present invention.

FIG. 16 is a side view illustrating the configuration of the blood pressure measurement device according to the modification of the present invention.

DESCRIPTION OF EMBODIMENTS

Figure 6:
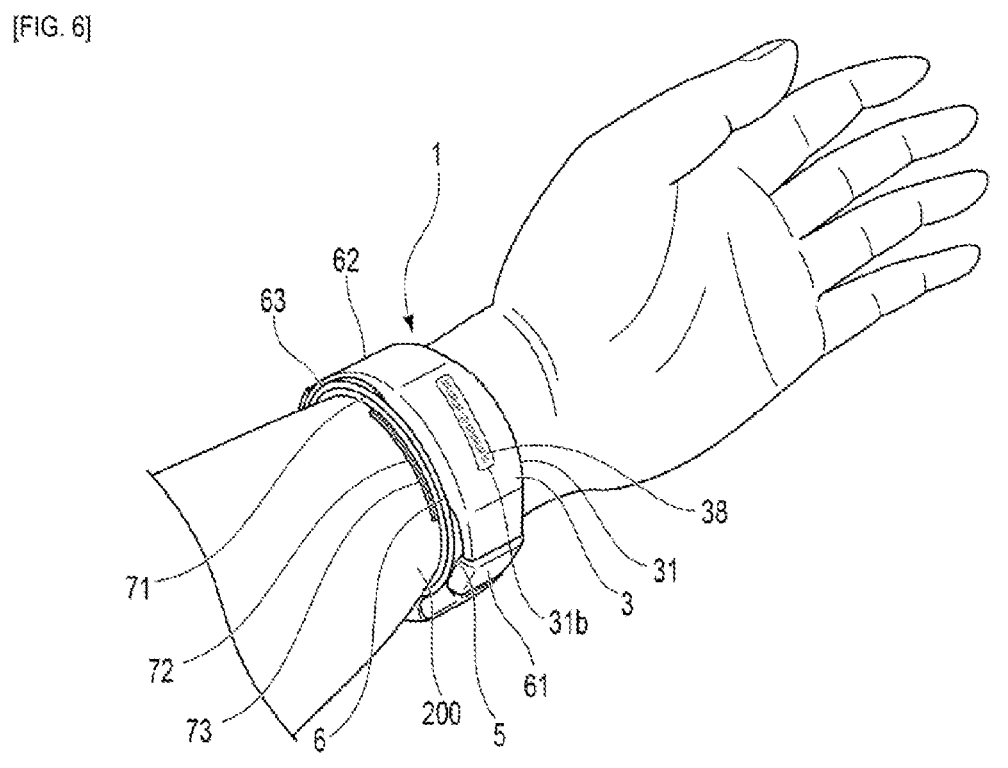

Hereinafter, an example of a blood pressure measurement device 1 according to an embodiment of the present invention will be described with reference to FIGS. 1 to 7.

FIG. 1 is an explanatory view illustrating a configuration of the blood pressure measurement device 1 in a state of being worn on a wrist 200. FIG. 2 is a side view illustrating a state in which a band 4 and a pressure measurement unit 3 used in the blood pressure measurement device 1 are separated from a watch body 2 used in the blood pressure measurement device 1. FIG. 3 is a block diagram illustrating a configuration of the blood pressure measurement device 1. FIG. 4 is a plan view illustrating a configuration of a cuff structure 6 used in the blood pressure measurement device 1 as viewed from the wrist 200 side. The cuff structure 6 illustrated in FIG. 4 is separated from a curler 5.

FIG. 5 is a plan view illustrating the configuration of the pressure measurement unit 3 and the band 4 as viewed from the side opposite to the wrist 200 side. FIG. 6 is an explanatory view illustrating a state in which the blood pressure measurement device 1 is worn on the wrist 200. FIG. 7 is a flowchart illustrating an example of the operation of the blood pressure measurement device 1.

The blood pressure measurement device 1 is an electronic blood pressure measurement device worn on a living body. The present embodiment will be described using an electronic blood pressure measurement device having an aspect of a wearable device attached to the wrist 200 of the living body.

As illustrated in FIGS. 1 to 3, the blood pressure measurement device 1 includes the watch body 2, the band 4 which includes the pressure measurement unit 3 and fixes the watch body 2 to the wrist 200, the curler 5 which is disposed between the band 4 and the wrist 200, and the cuff structure 6 which includes a pressing cuff 71 and a sensing cuff 73.

The blood pressure measurement device 1 is configured to be able to measure a pressure of an artery of a user, calculate a blood pressure value from the measured pressure, and display information including the calculated pressure value and time. In the blood pressure measurement device 1, the watch body 2 has a function in which information including the blood pressure value and time can be displayed, and the pressure measurement unit 3 of the band 4, which will be described below, has a function of measuring the pressure. The watch body 2 or the pressure measurement unit 3 has a function of calculating the blood pressure value based on a blood pressure measurement signal. In the present embodiment, as an example, the watch body 2 has a function of calculating the blood pressure value.

The watch body 2 is disposed on the back side of the wrist 200. The watch body 2 is configured to be able to display the time and the blood pressure value of the user. The watch body 2 is configured such that, for example, operation of starting blood pressure measurement can be input by the user and a command to start blood pressure measurement can be transmitted to the pressure measurement unit 3. For example, the watch body 2 is configured to be able to calculate the blood pressure value from the blood pressure measurement signal which is information necessary for blood pressure calculation received from the pressure measurement unit 3.

The watch body 2 includes, for example, a first case 11, a first display unit 12, an operating unit 13, a memory 14, a first communication unit 15, a first battery 16, and a first control unit (central processing unit) 17.

The first case 11 includes, for example, a cylindrical outer case 21 having an opening on the side opposite to the wrist 200 side, and a windshield 22 that covers the opening on the side opposite to the wrist 200 side of the outer case 21.

The outer case 21 is provided with a pair of lugs 23 provided at symmetrical positions in the circumferential direction of the outer peripheral surface.

For example, a spring rod 24 to which the band 4 is connected is provided between one pair of lugs 23. The spring rod 24 is an example of a connected portion to which the band 4 is connected. The other pair of lugs 23 is provided with a shaft portion 25 for folding back the band 4 wound around the wrist 200. The shaft portion 25 is formed in a rod shape, for example. The shaft portion 25 is, for example, a spring rod. The shaft portion 25 is provided, for example, in parallel to a direction orthogonal to a direction from the watch body 2 to the wrist 200 side.

The windshield 22 is, for example, a glass plate.

The first display unit 12 is electrically connected to the first control unit 17. The first display unit 12 is configured to be able to display date/time including the time of day. In addition, the first display unit 12 displays various kinds of information including the blood pressure value such as a systolic blood pressure and a diastolic blood pressure, and measurement results such as a heart rate. The first display unit 12 is disposed at a position facing the windshield 22. The first display unit 12 is electrically connected to the first control unit 17. The first display unit 12 is, for example, a liquid crystal display or an organic electroluminescence display.

The operating unit 13 is configured to be able to receive an instruction input from a user. For example, as illustrated in FIG. 1, the operating unit 13 includes a plurality of buttons 13*a* provided on the first case 11 and a sensor 13*b* that detects operation of the buttons 13*a*. For example, three buttons 13*a* are provided. The sensor 13*b* is electrically connected to the first control unit 17. The sensor 13*b* transmits a detection result to the first control unit 17.

The memory 14 is electrically connected to the first control unit 17. The memory 14 stores, for example, various programs for operating the watch body 2, a program for calculating a blood pressure value, and the like. The memory 14 stores the blood pressure value calculated by the first control unit 17.

The first communication unit 15 is electrically connected to the first control unit 17. The first communication unit 15 is configured to be able to wirelessly communicate with the pressure measurement unit 3. The first communication unit 15 uses, for example, Bluetooth (trade name).

The first battery 16 is electrically connected to the first control unit 17. The first battery 16 supplies electric power necessary for operation to each component of the watch body 2.

The first control unit 17 is configured by a single or a plurality of CPUs, controls the operation of the entire watch body 2, and calculates the blood pressure value. The first control unit 17 is electrically connected to the first display unit 12, the sensor 13*b* of the operating unit 13, the memory 14, the first communication unit 15, and the first battery 16. The first control unit 17 controls the first display unit 12. The first control unit 17 transmits a command to start blood pressure measurement from the first communication unit 15 to the pressure measurement unit 3 based on operation input to the operating unit 13. The first control unit 17 calculates the blood pressure value based on the blood pressure measurement signal transmitted from the pressure measurement unit 3. The first control unit 17 stores the calculated blood pressure signal in the memory 14.

As illustrated in FIGS. 1, 2, and 5, the band 4 includes the pressure measurement unit 3 and a band portion 60. The band 4 is configured to be detachable from and attachable to the watch body 2. In addition, the band 4 is configured such that the watch body 2 is disposed in the middle portion in the longitudinal direction of the band 4, and the sensing cuff 73 used for pressure measurement can be disposed in the region where the artery of the wrist 200 exists in a state where the watch body 2 is disposed on the back side of the wrist 200.

The band portion 60 is provided integrally with the pressure measurement unit 3, or provided separately from the pressure measurement unit 3 and connected to the pressure measurement unit 3, or a part of the band portion 60 is provided integrally with the pressure measurement unit 3 and the other part is provided separately from the pressure measurement unit 3 and connected to the pressure measurement unit 3. In the present embodiment, as an example, a configuration in which the band portion 60 is provided separately from the pressure measurement unit 3 and is used by being connected to the pressure measurement unit 3 will be described.

The band portion 60 includes, for example, a first band portion 61 and a second band portion 62. The first band portion 61 and the second band portion 62 are provided at symmetrical positions in the circumferential direction of a second case 31, which will be described below, of the pressure measurement unit 3, and are connected to the watch body 2. For example, the first band portion 61 is provided on one pair of lugs 23 and the spring rod 24 of the outer case 21 of the watch body 2, and the second band portion 62 is folded back at the shaft portion 25 provided between the other pair of lugs 23, whereby the band 4 is configured in an annular shape together with the watch body 2 and the pressure measurement unit 3.

The pressure measurement unit 3 includes, for example, the second case 31, a pump 32, a fluid path 33 that fluidly connects the pump 32 and the cuff structure 6, a valve 34, a pump drive circuit 35, a pressure sensor 36, a second communication unit 37, a second display unit 38, a second battery 39, and a second control unit 40.

In the present embodiment, for example, the pump 32, the fluid path 33, the valve 34, the pump drive circuit 35, the pressure sensor 36, the second communication unit 37, the second display unit 38, the second battery 39, and the second control unit 40 are an example of a configuration for measuring the pressure.

The second case 31 includes an outer case 31*a* having an opening on a surface opposite to the wrist 200 side, and a cover 31*b* covering the opening of the outer case 31*a*. The second case 31 is configured such that the band 4 can be connected thereto. The cover 31$b$ is formed of a transparent material through which the second display unit 38 can be visually recognized.

The pump 32 supplies compressed air to the cuff structure 6 via the fluid path 33.

The fluid path 33 is connected to the pump 32 and the cuff structure 6.

The valve 34 is electrically connected to the second control unit 40. The valve 34 is provided in the fluid path 33. The valve 34 seals the fluid path 33 when closed, and opens the fluid path 33 to the atmosphere when opened.

The pump drive circuit 35 is electrically connected to the second control unit 40. The pump drive circuit 35 drives the pump 32 under the control of the second control unit 40.

The pressure sensor 36 is electrically connected to the second control unit 40. The pressure sensor 36 detects the pressure of the sensing cuff 73. The pressure sensor 36 transmits a detection result to the second control unit 40.

The second communication unit 37 is electrically connected to the second control unit 40. The second communication unit 37 communicates with the first communication unit 15 of the watch body 2.

The second display unit 38 is electrically connected to the second control unit 40. The second display unit 38 is disposed to face the cover 31$b$. The second display unit 38 is, for example, a liquid crystal display or an organic electroluminescence display. The second display unit 38 displays the blood pressure value.

The second battery 39 is electrically connected to the second control unit 40. The second battery 39 supplies electric power to each component of the pressure measurement unit 3.

The second control unit 40 is an example of a control unit used in the pressure measurement unit 3. The second control unit 40 controls the valve 34, the pump drive circuit 35, the second communication unit 37, and the second display unit 38.

The first band portion 61 is formed in a shape elongated in one direction. In the present embodiment, the first band portion 61 is detachably attached to the spring rod 24. An end portion of the first band portion 61 is provided with an attachment portion 61$a$ that is detachable from and attachable to the spring rod 24.

The attachment portion 61$a$ has, for example, an opening, and is attached by disposing the spring rod 24 inside through the opening.

The first band portion 61 is configured to be adjustable in length, for example. The first band portion 61 includes, for example, a plurality of links 61$b$. The plurality of links 61$b$ are disposed side by side in one direction. The plurality of links 61$b$ are bendably connected along the circumferential direction of the wrist 200 of the user. The plurality of links 61$b$ are detachably and attachably configured. The length of the first band portion 61 are adjusted by adjusting the number of links 61$b$.

The second band portion 62 is formed of a material that can be curved along the wrist 200, for example, cloth. The second band portion 62 is provided with, for example, a fixing portion 63 that detachably and attachably fixes the portion folded back at the shaft portion 25 to the other portion of the second band portion 62. The fixing portion 63 is, for example, a hook-and-loop fastener.

The fixing portion 63 includes, for example, a hook portion 64 which is provided on one end side of the second band portion 62 and includes a plurality of hooks, and a loop portion 65 which is provided at a position closer to the pressure measurement unit 3 than the hook portion 64 and includes a plurality of loops. As an example, the second band portion 62 is detachably attached to the watch body 2 by fixing the hook portion 64 folded back at the shaft portion 25 to the loop portion 65.

In the above-described example, in the fixing portion 63, the hook portion 64 and the loop portion 65 are respectively configured in different regions of the surface of the second band portion 62, but the invention is not limited thereto. In another example, the fixing portion 63 may have a configuration in which a plurality of hooks and a plurality of loops are mixedly provided in the same predetermined region.

By adjusting the length of the first band portion 61, the band 4 configured as described above can fix the blood pressure measurement device 1 to the wrist 200 in an orientation in which the watch body 2 is disposed on the back side of the wrist 200 and the sensing cuff 73, which will be described below, of the cuff structure 6 is disposed in a region where an artery 210 of the wrist 200 exists.

As illustrated in FIGS. 1 and 2, the curler 5 is configured in a band-like shape that curves in such a manner as to follow along the circumferential direction of the wrist 200. The curler 5 is formed with one end and the other end spaced apart from each other. For example, the outer surface of the central portion of the curler 5 is fixed to the second case 31 of the pressure measurement unit 3 along the circumferential direction of the curler 5. For example, one end and the other end of the curler 5 are disposed at positions facing the pressure measurement unit 3.

The cuff structure 6 is fixed to the inner circumferential surface of the curler 5. The cuff structure 6 has at least a length to face the artery 210. As illustrated in FIGS. 1, 2, and 4, the cuff structure 6 includes, for example, the pressing cuff 71, a back plate 72, and the sensing cuff 73.

In the cuff structure 6, the back plate 72 is disposed on the pressing cuff 71, and the sensing cuff 73 is disposed on the back plate 72. In the cuff structure 6, the components disposed adjacent to each other are fixed to each other by, for example, a bonding layer. The bonding layer is formed of, for example, an adhesive or a double-sided tape.

The pressing cuff 71 is connected to the fluid path 33 of the pressure measurement unit 3. The pressing cuff 71 is fluidly connected to the pump 32 by being connected to the fluid path 33. The pressing cuff 71 is configured in a band-like shape extending in one direction. The pressing cuff 71 extends, for example, from one end to the other end of curler 5.

As illustrated in FIG. 4, the pressing cuff 71 includes an air bag 81 and a connection portion 84 connected to the fluid path 33 of the pressure measurement unit 3. Here, the air bag 81 is a bag-like structure, and in the present embodiment, since the blood pressure measurement device 1 is configured to use air by the pump 32, the description will be made using the air bag. However, in a case where a fluid other than air is used, the bag-like structure may be any fluid bag which is inflated by the fluid.

The connection portion 84 is provided on a surface of the air bag 81 facing the curler 5. The connection portion 84 is configured to be connectable to the fluid path 33 via the curler 5.

As illustrated in FIG. 4, the back plate 72 is formed in a plate shape elongated in one direction. The back plate 72 is fixed to the outer surface of the pressing cuff 71 on the wrist 200 side. The back plate 72 is formed to have a length to cover the palm side of the wrist 200, for example. The back plate 72 transfers the pressing force from the pressing cuff 71 to the back plate 72 side main surface of the sensing cuff 73 in a state where the back plate 72 is extending along the shape of the wrist 200.

The back plate 72 has shape followability. Here, "shape followability" refers to a function in which the back plate 72 can be deformed in such a manner as to follow the shape of a contacted portion of the wrist 200 to be disposed. This contacted portion of the wrist 200 refers to a region of the wrist 200 that faces the back plate 72. This contact includes both direct contact and indirect contact with the sensing cuff 73 interposed therebetween. For example, as illustrated in FIG. 4, the back plate 72 has a plurality of grooves 72*a* extending in a direction orthogonal to the longitudinal direction of the back plate 72 on both main surfaces of the back plate 72.

The sensing cuff 73 is fixed to a surface of the back plate 72 on the wrist 200 side. The length of the sensing cuff 73 in the longitudinal direction is set to a length that allows the sensing cuff 73 to be in contact with a region where at least one of a radial artery 211 and an ulnar artery 212, which are the arteries 210 of the wrist 200, exists.

For example, the sensing cuff 73 is formed in the same shape as that of the back plate 72 or a shape that is smaller than that of the back plate 72, in the longitudinal direction and the width direction of the back plate 72. The sensing cuff 73 is pressed by the inflated pressing cuff 71 toward the wrist 200 side with the back plate 72 interposed therebetween.

The sensing cuff 73 is, for example, fluidly connected to the pressing cuff 71 via a throttle. A throttle 94 is, for example, an orifice.

As illustrated in FIG. 4, the sensing cuff 73 includes, for example, one air bag 91 and a connection portion 93. Here, the air bag 91 is a bag-like structure, and in the present embodiment, the blood pressure measurement device 1 is configured to use air with the pump, and thus the present embodiment will be described using the air bag. However, in a case where a fluid other than air is used, the bag-like structure may be any fluid bag that is inflated by the fluid. The connection portion 93 is fluidly connected to the pressing cuff 71. For example, the throttle 94 is provided in the connection portion 93 or a flow path that connects the connection portion 93 and the air bag 81 of the pressing cuff 71.

In the blood pressure measurement device 1 configured as described above, the length of the first band portion 61 is adjusted such that the watch body 2 is disposed on the back side of the wrist 200 and the sensing cuff 73 is disposed in a region where the artery of the wrist 200 exists.

Next, an example in which the user attaches the blood pressure measurement device 1 to the wrist 200 will be described. FIG. 6 illustrates an example in which the user wears the blood pressure measurement device 1 on the wrist 200.

First, the user releases the fixing of the second band portion 62 by the fixing portion 63, and adjusts the annular space formed by the watch body 2, the pressure measurement unit 3, and the band 4 to a size with which the wrist 200 can be inserted into the annular space.

Next, as illustrated in FIG. 6, the user inserts the wrist 200 into the annular space formed by the watch body 2, the pressure measurement unit 3, and the band 4.

Next, the user adjusts the position of the blood pressure measurement device 1 so that the watch body 2 is positioned on the back side of the wrist 200 and the pressure measurement unit 3 is positioned on the palm side of the wrist 200.

Next, the user presses the sensing cuff 73 against the region of the wrist 200 where the artery exists by pulling the second band portion 62, and fixes the hook portion 64 to the loop portion 65. The blood pressure measurement device 1 is thus attached to the wrist 200 by this procedure.

Next, an example of the operation of the blood pressure measurement device 1 will be described. FIG. 7 is a flowchart illustrating an example of the operation. The user operates the buttons 13*a* of the operating unit 13 to input a command corresponding to the start of blood pressure measurement (step S1).

When the first control unit 17 determines that the command corresponding to the start of the blood pressure value measurement is input based on the detection result of the sensor 13*b* of the operating unit 13, the first control unit 17 initializes the region for processing of the memory 14, and transmits the command to start blood pressure measurement to the second communication unit 37 of the pressure measurement unit 3 by the first communication unit 15 (step S2).

When the second control unit 40 of the pressure measurement unit 3 receives the command to start blood pressure measurement by the second communication unit 37, the second control unit 40 stops the pump 32 via the pump drive circuit 35 and opens the valve 34 to discharge the air in the pressing cuff 71. Subsequently, the second control unit 40 drives the pump 32 via the pump drive circuit 35, closes the valve 34, and starts pressurization of the pressing cuff 71 (step S3).

A part of the compressed air supplied to the pressing cuff 71 is supplied to the sensing cuff 73 via the throttle 94. The second control unit 40 controls the pump 32 based on the detection result of the pressure sensor 36, controls the compressed air to be supplied to the pressing cuff 71, and gradually inflates the pressing cuff 71 and the sensing cuff 73.

The second control unit 40 transmits the detection result of the pressure sensor 36 to the first communication unit 15 of the watch body 2 via the second communication unit 37 in the pressurization process.

When the first communication unit 15 receives the detection result of the pressure sensor 36, the first control unit 17 calculates the blood pressure value (step S4). Further, the first control unit 17 acquires a pulse wave signal from the detection result of the pressure sensor 36.

The first control unit 17 determines whether or not the blood pressure value can be determined (step S5). The case where the blood pressure value cannot be determined is a case where the pressure of the sensing cuff 73 does not reach an upper limit value of the measurement of the blood pressure.

When the blood pressure value cannot be determined due to lack of data, that is, when the pressure of the sensing cuff 73 has not reached the upper limit value (NO in step S5), the first control unit 17 repeats steps S3 to S5.

When the first control unit 17 can determine the pressure value (YES in step S5), the first control unit 17 transmits a command to stop the pump 32 to the second communication unit 37 by the first communication unit 15. When the second control unit 40 receives the command to stop the pump 32 by the second communication unit 37, the second control unit 40 stops the driving of the pump 32, opens the valve 34, and exhausts air from the sensing cuff 73 and the pressing cuff 71 (step S6). In addition, the second control unit 40 transmits the stop of the driving of the pump 32 to the first communication unit 15 by the second communication unit 37.

Next, the first control unit 17 transmits the blood pressure value to the second communication unit 37 by the first communication unit 15 and displays the blood pressure value on the first display unit 12 (step S7). When the blood pressure value is received by the second communication unit 37, the second control unit 40 displays the blood pressure value on the second display unit 38 (step S8).

According to the blood pressure measurement device 1 configured as described above, the watch body 2 and the band 4 including the pressure measurement unit 3 are provided, and thus a configuration for exerting a function of displaying information including the time and the blood pressure value and a configuration for exerting a function of measuring the blood pressure can be separated. Furthermore, the watch body 2 includes the first communication unit 15, the pressure measurement unit 3 includes the second communication unit 37, and the communication units 15 and 37 are configured to be able to wirelessly communicate with each other. Therefore, it is not necessary to provide wiring for communication between the watch body 2 and the pressure measurement unit 3.

Further, by dividing the functions of the blood pressure measurement device 1 into the watch body 2 and the pressure measurement unit 3, the pump 32 and the pressure sensor 36 are not accommodated in the watch body 2, and thus it is also possible to prevent the watch body 2 from being increased in size.

Furthermore, since the distance from the pump 32 to the cuff structure 6 can be shortened, the cuff structure 6 can be efficiently inflated.

Furthermore, since the sensing cuff 73 is fixed to the wrist 200 side of the pressure measurement unit 3, the pressure measurement unit 3 is disposed on the palm side of the wrist 200, whereby the sensing cuff 73 can be disposed in a region of the wrist 200 where the artery exists. That is, by using the pressure measurement unit 3 as a mark, the sensing cuff 73 can be easily disposed in the region of the wrist 200 where the artery exists.

Further, since the band 4 is detachably attached to the watch body 2, the band 4 can be attached to various watch bodies 2.

Further, the length of the first band portion 61 can be adjusted. Therefore, by adjusting the length of the first band portion 61, it is possible to dispose the watch body 2 on the back side of the wrist 200 and dispose the pressure measurement unit 3 on the palm side of the wrist 200, according to the circumferential length of the wrist 200 of the user.

Further, in the second band portion 62, the length of the second band portion 62 between the pressure measurement unit 3 and the watch body 2 can be adjusted. Therefore, by adjusting the length of the second band portion 62 between the pressure measurement unit 3 and the watch body 2, the band 4 can be suitably tightened in accordance with the circumferential length of the wrist 200, and thus the accuracy of blood pressure measurement can be improved.

Further, the watch body 2 is provided with the first battery 16, and the pressure measurement unit 3 is provided with the second battery 39. Therefore, it is not necessary to provide wiring for power supply outside the watch body 2 and the blood pressure measurement device.

Further, since the first control unit 17 of the watch body 2 is used as the control unit for calculating the blood pressure value, the function of the second control unit 40 of the pressure measurement unit 3 can be suppressed to be small. Therefore, since the second control unit 40 can be miniaturized, the pressure measurement unit 3 can be miniaturized.

Furthermore, since the pressure measurement unit 3 includes the second display unit 38, the blood pressure value can also be visually recognized in the pressure measurement unit 3.

Furthermore, since the watch body 2 is configured to include the operating unit 13 to which the operation of starting the blood pressure measurement is input, the pressure measurement unit 3 can be miniaturized.

As described above, according to the blood pressure measurement device 1 of the present embodiment, the watch body 2 that displays information including the time and the blood pressure value, and the pressure measurement unit 3 that measures the pressure can be separated.

In the above-described example, the configuration in which the pressure measurement unit 3 includes one second case 31 and the pump 32, the fluid path 33, the pump drive circuit 35, the pressure sensor 36, the second communication unit 37, the second display unit 38, the second battery 39, and the second control unit 40 are provided in the second case 31 has been described as an example, but the invention is not limited thereto.

In another example, the pressure measurement unit 3 may include a plurality of cases, and the pump 32, the fluid path 33, the pump drive circuit 35, the pressure sensor 36, the second communication unit 37, the second display unit 38, the second battery 39, and the second control unit 40 may be dispersed and accommodated in a plurality of the second cases 31.

As an example thereof, as illustrated in FIGS. 8 to 10, the pressure measurement unit 3 may be configured to include two cases. FIG. 8 is a side view illustrating the configuration of the blood pressure measurement device 1 according to the modification in a state where the pressure measurement unit 3 and the band 4 are separated from the watch body 2. FIG. 9 is a block diagram illustrating the configuration of the blood pressure measurement device 1 according to the modification. FIG. 10 is a plan view illustrating the configuration of the pressure measurement unit 3 and the band 4 used in the blood pressure measurement device 1 according to the modification as viewed from the side opposite to the wrist 200 side.

As illustrated in FIGS. 8 to 10, in the modification, the pressure measurement unit 3 includes, as two cases, a sub-case 101 in addition to the second case 31. For example, the pump 32, the fluid path 33, the pressure sensor 36, and the second display unit 38 are accommodated in the second case 31. For example, the pump drive circuit 35, the second communication unit 37, the second battery 39, and the second control unit 40 are accommodated in the sub-case 101.

In addition, in another example, the pressure measurement unit 3 may be configured to include three cases as in a modification illustrated in FIGS. 11 to 13. FIG. 11 is a side view illustrating the configuration of the blood pressure measurement device 1 according to the modification in a state where the pressure measurement unit 3 and the band 4 are separated from the watch body 2. FIG. 12 is a block diagram illustrating the configuration of the blood pressure measurement device 1 according to the modification. FIG. 13 is a plan view illustrating the configuration of the pressure measurement unit 3 and the band 4 used in the blood pressure measurement device 1 according to the modification as viewed from the side opposite to the wrist 200 side.

As illustrated in FIGS. 11 to 13, in the modification, the pressure measurement unit 3 includes, as three cases, the sub-case 101 and a sub-case 102 in addition to the second case 31. For example, the pump 32, the fluid path 33, the pressure sensor 36, and the second display unit 38 are accommodated in the second case 31. For example, the pump drive circuit 35, the second communication unit 37, and the second control unit 40 are accommodated in the sub-case 101. The second battery 39 is accommodated in the sub-case 102.

Further, in the above-described example, the configuration in which the sensing cuff 73 is fluidly connected via the pressing cuff 71 has been described as an example, but the invention is not limited thereto. In another example, as illustrated in FIG. 14, the sensing cuff 73 may be directly connected to the fluid path 33. In the case of this configuration, the connection portion 93 is connected to the fluid path 33.

In the example described above, the blood pressure measurement device 1 has a configuration in which the watch body 2 includes the first control unit 17 and the memory 14 which are components necessary for calculating the blood pressure based on the detection result of the pressure sensor 36, but the invention is not limited thereto.

In another example, the watch body 2 may be configured to be able to calculate the blood pressure based on the detection result of the pressure sensor 36. For example, the watch body 2 may include a memory necessary for calculating the blood pressure based on the detection result of the pressure sensor 36, and the blood pressure may be calculated by the memory and the second control unit 40. In the case of this configuration, the blood pressure value may be calculated by the pressure measurement unit 3, the blood pressure value may be transmitted to the watch body 2, and the blood pressure value may be displayed on the first display unit 12. In the case of this configuration, the watch body 2 does not need to have a function of calculating the blood pressure based on the detection result of the pressure sensor 36, and has a function of receiving and displaying the information of the blood pressure value from the outside. Therefore, various watch bodies 2 can be used.

In addition, in the above-described example, a configuration in which the first band portion 61 includes the plurality of links 61*b* as a length-adjustable configuration has been described as an example, but the invention is not limited thereto. In another example, as illustrated in FIG. 15, the shaft portion 25 may be provided between the pair of lugs 23 of the second case 31 of the watch body 2, and the length of the first band portion 61 may be adjustable by adjusting the folding position at the shaft portion 25. The first band portion 61 folded back at the shaft portion 25 may be fixed to another portion of the first band portion 61 by a detachable and attachable fixing portion 63 such as a hook-and-loop fastener.

In the above-described example, the configuration in which the pressure measurement unit 3 and the band 4 are configured as separate bodies and the band 4 is connected to the second case 31 of the pressure measurement unit 3 has been described as an example, but the present invention is not limited thereto. In other examples, the second case 31 and the band 4 may be integrated instead of being separately configured and connected. Alternatively, a part of the band 4 may be integrated with the second case 31, and the other part of the band 4 may be formed separately from the second case 31 and connected to the second case 31.

In addition, the pressure measurement unit 3, the band 4, the curler 5, and the cuff structure 6 may not be configured to be separately configured and connected, but may be integrated.

In the above-described example, the operating unit 13 of the watch body 2 is configured to be able to receive input of the operation of starting the blood pressure measurement can be input, but the invention is not limited thereto. In another example, the pressure measurement unit 3 may include an operating unit to which operation to start blood pressure measurement can be input.

In the above-described example, the configuration in which the pressure measurement unit 3 includes the second display unit 38 has been described as an example, but the invention is not limited thereto. For example, the pressure measurement unit 3 may not include the second display unit 38.

In the above-described example, the configuration in which the blood pressure measurement device 1 includes the curler 5 has been described as an example, but the invention is not limited thereto. In another example, the blood pressure measurement device 1 may not include the curler 5. The blood pressure measurement device 1 according to the modification will be described with reference to FIG. 16. FIG. 16 illustrates, as an example, the blood pressure measurement device 1 in which the pressure measurement unit 3 includes three cases 31, 101, and 102.

As illustrated in FIG. 16, in the case where the blood pressure measurement device 1 does not include the curler 5, for example, the pressing cuff 71 is fixed to the surface of the second case 31 of the pressure measurement unit 3 on the wrist 200 side. Further, in a case where the blood pressure measurement device 1 is configured not to include the curler 5, the blood pressure measurement device 1 may include a fixing portion 104 for fixing the cuff structure 6 in a state of being wound around the wrist 200 at a stage before the band 4 is wound around the wrist 200. For example, the fixing portion 104 fixes both ends of the pressing cuff 71 wound around the wrist 200. The fixing portion is, for example, a hook-and-loop fastener or a snap fit.

Note that the present invention is not limited to the above-described embodiments, and various modifications can be made in an implementation stage without departing from the gist. Further, embodiments may be carried out as appropriate in a combination, and combined effects can be obtained in such case. Further, the various inventions are included in the embodiment, and the various inventions may be extracted in accordance with combinations selected from the plurality of disclosed constituent elements. For example, in a case where the problem can be solved and the effects can be obtained even when some constituent elements are removed from the entire constituent elements given in the embodiment, the configuration obtained by removing the constituent elements may be extracted as an invention.

REFERENCE NUMERALS LIST

1 Blood pressure measurement device
2 Watch body
3 Pressure measurement unit
4 Band
5 Curler
6 Cuff structure
11 First case
12 First display unit
13 Operating unit
13*a* Button
13*b* Sensor
14 Memory
15 First communication unit
16 First battery

17 First control unit
21 Outer case
22 Windshield
23 Lug
24 Spring rod
25 Shaft portion
31 Second case
31*a* Outer case
31*b* Cover
32 Pump
33 Fluid path
34 Valve
35 Pump drive circuit
36 Pressure sensor
37 Second communication unit
38 Second display unit
39 Second battery
40 Second control unit
60 Band portion
61 First band portion
61*a* Attachment portion
61*b* Link
62 Second band portion
63 Fixing portion
64 Hook portion
65 Loop portion
71 Pressing cuff
72 Back plate
72*a* Groove
73 Sensing cuff
81 Air bag
84 Connection portion
86 Sheet member
91 Air bag
93 Connection portion
96 Sheet member
101 Sub-case
102 Sub-case
200 Wrist
210 Artery
211 Radial artery
212 Ulnar artery

What is claimed is:

1. A blood pressure measurement device configured to be worn on a wrist of a user, the blood pressure measurement device comprising:

a watch body including a display unit and a first wireless communication circuit configured to transmit and receive signals, the display unit being configured to display information including time and a blood pressure value, the watch body configured to be disposed on a back side of said wrist of a user;

a band including a pressure measurement unit and a band portion, the pressure measurement unit including a second wireless communication circuit configured to transmit and receive signals from the watch body, a pump, and a sensor configured to detect a pressure, the band portion being provided in the pressure measurement unit and connected to the watch body;

a curler formed in a band shape curved along a circumferential direction of said wrist of a user, one end and another end of the curler being separated from each other;

a cuff provided on an inner circumferential surface of the curler and fluidly connected to the pump and the sensor; and a control unit provided in the watch body or the pressure measurement unit and configured to calculate a blood pressure value based on a detection result of the sensor, wherein the pressure measurement unit is fixed to an outer surface of a central portion in a circumferential direction of the curler.

2. The blood pressure measurement device according to claim 1, wherein the cuff includes a sensing cuff disposed in a region where an artery of the wrist exists, and the sensing cuff is disposed on a side of the wrist of the pressure measurement unit.

3. The blood pressure measurement device according to claim 1, wherein the band is detachably attached to the watch body.

4. The blood pressure measurement device according to claim 3, wherein the band portion is configured such that a length between the pressure measurement unit and the watch body can be adjusted.

5. The blood pressure measurement device according to claim 1, wherein the control unit is provided in the watch body.

6. The blood pressure measurement device according to claim 1, wherein the pressure measurement unit includes a pressure measurement unit display unit configured to display a blood pressure value.

7. The blood pressure measurement device according to claim 1, wherein the watch body or the pressure measurement unit includes an input interface comprising a plurality of buttons and a sensor that detects operation of the buttons to which operation of starting blood pressure measurement is input.

* * * * *